(12) United States Patent
Inoue et al.

(10) Patent No.: US 7,393,505 B2
(45) Date of Patent: Jul. 1, 2008

(54) PROTON CONDUCTOR GAS SENSOR

(75) Inventors: Tomohiro Inoue, Minoo (JP); Hideki Okoshi, Minoo (JP); Kazunari Kaneyasu, Minoo (JP)

(73) Assignee: Figaro Engineering Inc., Osaka (JP)

( * ) Notice: Subject to any disclaimer, the term of this patent is extended or adjusted under 35 U.S.C. 154(b) by 0 days.

(21) Appl. No.: 10/522,707

(22) PCT Filed: Jul. 28, 2003

(86) PCT No.: PCT/JP03/09553

§ 371 (c)(1),
(2), (4) Date: Aug. 10, 2005

(87) PCT Pub. No.: WO2004/011923

PCT Pub. Date: Feb. 5, 2004

(65) Prior Publication Data

US 2006/0120924 A1   Jun. 8, 2006

(30) Foreign Application Priority Data

| Jul. 31, 2002 | (JP) | ............................ 2002-222731 |
| Nov. 18, 2002 | (JP) | ............................ 2002-333273 |
| Jan. 27, 2003 | (JP) | ............................ 2003-17145 |

(51) Int. Cl.
*G01N 7/00* (2006.01)
*G01N 21/00* (2006.01)
*G01N 27/00* (2006.01)
*G01N 31/00* (2006.01)
*G01N 33/00* (2006.01)

(52) U.S. Cl. ............................ 422/83; 422/90; 422/98; 204/424; 204/431; 204/432

(58) Field of Classification Search .................. 422/83, 422/90, 98; 204/424, 431, 432
See application file for complete search history.

(56) References Cited

U.S. PATENT DOCUMENTS

| 4,560,444 | A | * | 12/1985 | Polak et al. .................. 205/783 |
| 4,689,122 | A | * | 8/1987 | Polak et al. .................. 205/783 |
| 4,820,386 | A | | 4/1989 | La Conti |
| 5,302,274 | A | * | 4/1994 | Tomantschger et al. ...... 204/412 |
| 5,573,648 | A | * | 11/1996 | Shen et al. .................... 204/412 |
| 5,841,021 | A | * | 11/1998 | De Castro et al. ............. 73/23.2 |
| 6,948,352 | B2 | * | 9/2005 | Rabbett et al. ................ 73/1.04 |
| 2004/0134780 | A1 | * | 7/2004 | Inoue et al. ................... 204/424 |

FOREIGN PATENT DOCUMENTS

| EP | 762117 A3 | 3/1997 |
| JP | 12-146908 A | 5/2000 |
| JP | 2002-350393 A | 12/2002 |

* cited by examiner

*Primary Examiner*—Brian J Sines
(74) *Attorney, Agent, or Firm*—Rothwell, Figg, Ernst & Manbeck

(57) ABSTRACT

A proton conductor gas sensor whose durability at high temperature is enhanced by using gel not converted to sol even at high temperature in a water reservoir. Fine particles of silica are gelled by adding water thereto and agitating the mixture under shear force. The thus obtained gel (34) is placed in a water reservoir of proton conductor gas sensor (2) and fed through steam introduction port (30) to MEA (10).

5 Claims, 10 Drawing Sheets

PROTON CONDUCTOR GAS SENSOR

CROSS REFERENCE TO RELATED APPLICATION

This application is a 35 USC § 371 National Phase Entry Application from PCT/JP03/009553, filed Jul. 28, 2003, and designating the U.S.

FIELD OF THE INVENTION

The present invention relates to a proton conductor gas sensor, and in particular, relates to a water reservoir thereof.

BACKGROUND OF THE INVENTION

| | |
|---|---|
| Document 1 | Unexamined Japanese patent 2000-146908 (U.S. Pat. No. 6200443) |
| Document 2 | U.S. Pat. No. 5650,054 |
| Document 3 | U.S. Pat. No. 4820,386 |
| Document 4 | Unexamined Japanese patent 2002-350393 |

Documents 1 through 3 disclose structures of proton conductor gas sensors having water reservoirs. In document 1, a sensing electrode and a counter electrode are provided on both sides of a proton conductive membrane to form a membrane electrode assembly (MEA), and the MEA is sandwiched with hydrophobic and porous electro-conductive carbon sheets. The upper and lower carbon sheets are interposed by a pair of metal plates having openings, and they are fixed in a metal can with a water reservoir. Water vapor from the water reservoir moves through the opening of the lower metal plate and, via the hydrophobic carbon sheet, reaches the counter electrode. The ambient atmosphere diffuses through the opening of the upper metal plate to the sensing electrode. Thus, necessary electrode reactions take place at both the sensing electrode and the counter electrode, and the electromotive force, the current value, etc. enable the detection of a gas in the ambient atmosphere.

If liquid water, however, is contained in the water reservoir, for example, with a sudden rise in the water reservoir temperature, the air in the water reservoir swells to extrude water. A countermeasure against this is to gelate water as taught in document 3. If a water absorbing polymer such as polyacrylic one is used for the reservoir, it may contaminate the MEA because it contains metal ions such as Na+. Hence the present inventors considered using a natural polymer as a gelling agent but found that such a gel is solated at elevated temperature to affect the sensor output. Accordingly, a gel having a low content of metal ions and not being solated at elevated temperature is required. Moreover, to extend the service life of the water reservoir, a gelling agent that can hold a large amount of water is desirable.

In document 2 a lower part of a metal can is used as a water reservoir, a washer is arranged above the lower part of the metal can, an MEA is placed on the washer, and a cap is arranged on the upper side of the MEA. As a result, the metal can is connected to the counter electrode, and the cap is connected to the sensing electrode.

SUMMARY OF THE INVENTION

Objects of the Invention

One object of the present invention is to enhance the durability at elevated temperature of proton conductor gas sensors with a gel for the water reservoir not solated even at elevated temperature.

Another object of the present invention is to provide a preferable composition of the gelling agent.

Another object of the present invention is to make a hydrophobic carbon sheet between the MEA and the metal plate on the water reservoir redundant.

Another object of the present invention is to provide a gas distribution channel by the metal plate on the water reservoir, when the hydrophobic carbon sheet between the MEA and the metal plate is eliminated.

Another object of the present invention is to minimize the dispersion in the proton conductor gas sensor outputs.

Still another object of the present invention is to provide a new structure of proton conductor gas sensors.

Features of the Invention

In the present invention, a proton conductor gas sensor wherein water vapor is supplied from a water reservoir to a sensor body having an MEA comprising a proton conductive membrane, a sensing electrode, and a counter electrode, the sensor is characterized in that the water reservoir reserves gel comprising water as a dispersion medium and inorganic fine particles as a dispersoid dispersed in the water.

The composition of the inorganic fine particles is discretionary. Preferably, the inorganic fine particles are silica fine particles that can be produced easily. And in particular, as a gelling agent having a large water-holding capacity, the so-called dry method silica, obtained by decomposing a silicon compound in vapor phase, is desirable.

Moreover, preferably, the sensor body having, in addition to the MEA, a metal plate having an opening towards the water reservoir and contacting the MEA directly. As for the kind of the metal plate, from the viewpoint of corrosion resistance against sulfonic acid group, etc. in the proton conductive membrane, stainless steel or titanium or titanium alloy is preferable.

Particularly preferably, the metal plate has concaves and convexes on its surface towards the MEA for gas distribution. The configurations of the concaves and convexes are discretionary, and for example, a gas channel is provided between the circumferential side and the central side of the metal plate.

Advantages of the Invention

In the present invention, gelated water is used in the water reservoir of the proton conductor gas sensor, and inorganic fine particles, such as silica or alumina, are used as its gelling agent. The gelling agent has a primary particle diameter of, for example, from about 5 to 50 nm, and when water is gelated, the primary particles will link with each other in chains to form a network structure or a mesh structure. Water is retained in the network, and the space between chains of the gelling agent is filled with water, the dispersion medium. The chains of the gelling agent are present in the water of continuous phase in the form of network, and the water is gelated by this network.

Such gelling agents include, for example, fine particles of silica, alumina, or titania. In particular, it is preferable to use a gelling agent produced by the so-called dry method where the fine particles are produced by decomposing a compound of, for example, silicon or aluminum or titanium in vapor phase. In a gelling agent obtained by the dry method, the content of metal ions can be minimized extremely, for example, down to several ppm or under. When the gelling agent is produced by a conventional wet method, if the production conditions are adequately chosen, the metal ion content can be reduced extremely. This is because, while gelling agents comprising synthetic polymers, such as acrylic acid polymer, gelate with osmotic pressure according to the metal ion, the gelling agents used in the invention do not depend upon the osmotic pressure. Moreover, the gels made from inorganic fine particle gelling agents are not solated at around 70° C. in contrast to the gels from a synthetic polymer or a natural polymer gelling agent. Accordingly, the contamination of the MEA by the metal ions does not happen, and the durability of the gas sensor at elevated temperature is enhanced. Furthermore, as no nutrients are contained in the gel, miscellaneous bacteria will not grow, and therefore, no antiseptic agent is needed. Thus in turn, the contamination of the MEA caused by an antiseptic agent does not happen.

When inorganic fine particles made by the dry method are used as the gelling agent, a large amount of water can be retained by a small amount of the gelling agent. For example, in the case of a dry method silica, the amount of the gelling agent in the gel can be set at about 10 to 30 wt %, and in particular, at about 18 to 25 wt %, and the greater part of the gel is water. Conventional silica gel is produced by a wet method, where, for example, sodium silicate is hydrolyzed in water, while adjusting the primary particle diameter and specific surface area. The wet method silica gel is used as, for example, adsorbent, and the amount of water it can hold is 10 wt % or less of the dry weight of the gel. Only a small amount of water can be contained in the water reservoir, and in turn, the service life of the gas sensor or the interval of water replenishment is short.

The production method of a gelling agent is discretionary. It can be produced by pyrolysis of a vapor phase compound of silicon, for example, pyrolysis of $SiCl4$ or $SiHCl3$ with steam or the like. Fine particles that are obtained by pyrolysis in vapor phase are substantially spherical and extremely small in particle diameter, for example, about 5 to 50 nm. As for the gelling agent composition, fine particles obtained by pyrolysis of a vapor-phase compound are preferable, and in particular, a gelling agent comprising silica fine particles produced by pyrolysis of $SiCl4$ or the like is preferable.

When water in the water reservoir is gelated, liquid water in it does not reach the MEA, and therefore, the hydrophobic carbon sheet between the MEA and the metal plate above the water reservoir becomes redundant. The hydrophobic carbon sheet is an expensive member for fuel cell, and if this is made redundant, the cost of the proton conductor gas sensor is reduced.

When a gas other than hydrogen is to be detected, for example, CO, $NH3$, or $H2S$ is to be detected, it is necessary to reduce the sensor's hydrogen sensitivity. The present inventors have found that, when the counter electrode of the MEA is made to contact directly the metal plate on the water reservoir, the relative sensitivity to hydrogen in relation to CO or the like is increased. The present inventors have also found that, when the surface of the metal plate is provided with concaves and convexes, the relative sensitivity to hydrogen is reduced.

If the counter electrode of the MEA is arranged towards the water reservoir, if the counter electrode is made to contact directly the metal plate, and if the surface of the metal plate is mirror-finished or flat and smooth it is hard to provide a hydrogen diffusion channel between the counter electrode and the metal plate. In contrast to it, when the surface of the metal plate is provided with concaves and convexes, such concaves and convexes will provide diffusion channels for hydrogen reaching the counter electrode substantially over the entire surface of the electrode. As a result, the hydrogen sensitivities at the both electrodes cancel with each other, and thus the hydrogen sensitivity of the gas sensor in total is reduced. When the sensing electrode is provided towards the water reservoir, a gas to be detected can be distributed substantially all over the surface of the sensing electrode, similarly by the concaves and convexes on the surface of the metal plate.

The inventors have experienced that the dispersion of the sensitivities among the proton conductor gas sensors was caused by, for example, that the proton conductive membrane or its electrodes were not positioned in the right position, and that gas diffusion to the proton conductive membrane was not controlled uniformly. Of such causes, the dislocation of the proton conductive membrane or the electrodes results in remarkable variations in the sensor outputs. And they were beyond an allowable dispersion of the sensor outputs. Non-uniform control of the gas diffusion similarly causes dispersion of the sensor outputs, because they are proportional to the gas provided by the diffusion. And this factor was the largest cause of dispersion of the sensor outputs.

It is difficult to control the diffusion even by providing a cap with a gas introducing hole of a small diameter. It, however, is relatively easy to control the diffusion by providing a metal plate in addition to the cap and providing the metal plate with another gas introducing hole of an accurate diameter. Accordingly, in the present invention, the output dispersion of the gas sensors can be minimized.

In the proton conductor gas sensor according to the present invention, an MEA and its pair of upper and lower conductive plates are set in a ring-shaped member of resin, and they are pressed from above and below by flanges to be fixed. In the case of this gas sensor, since at least one flange can be formed by thermally deforming a ring-shaped member, no caulking is required. Accordingly, there will be no displacement of the MEA resulting from caulking, and no screwing is required. Hence a small-sized and low-cost proton conductor gas sensor can be obtained.

In the production method of the proton conductor gas sensor, for example, an MEA and a pair of upper and lower conductive plates are set in a ring-shaped member of resin, and this member is thermally deformed to sandwich the pair of upper and lower conductive plates. Thus a proton conductor gas sensor can be produced without any caulking or screwing.

BEST EMBODIMENT

Figure 1:
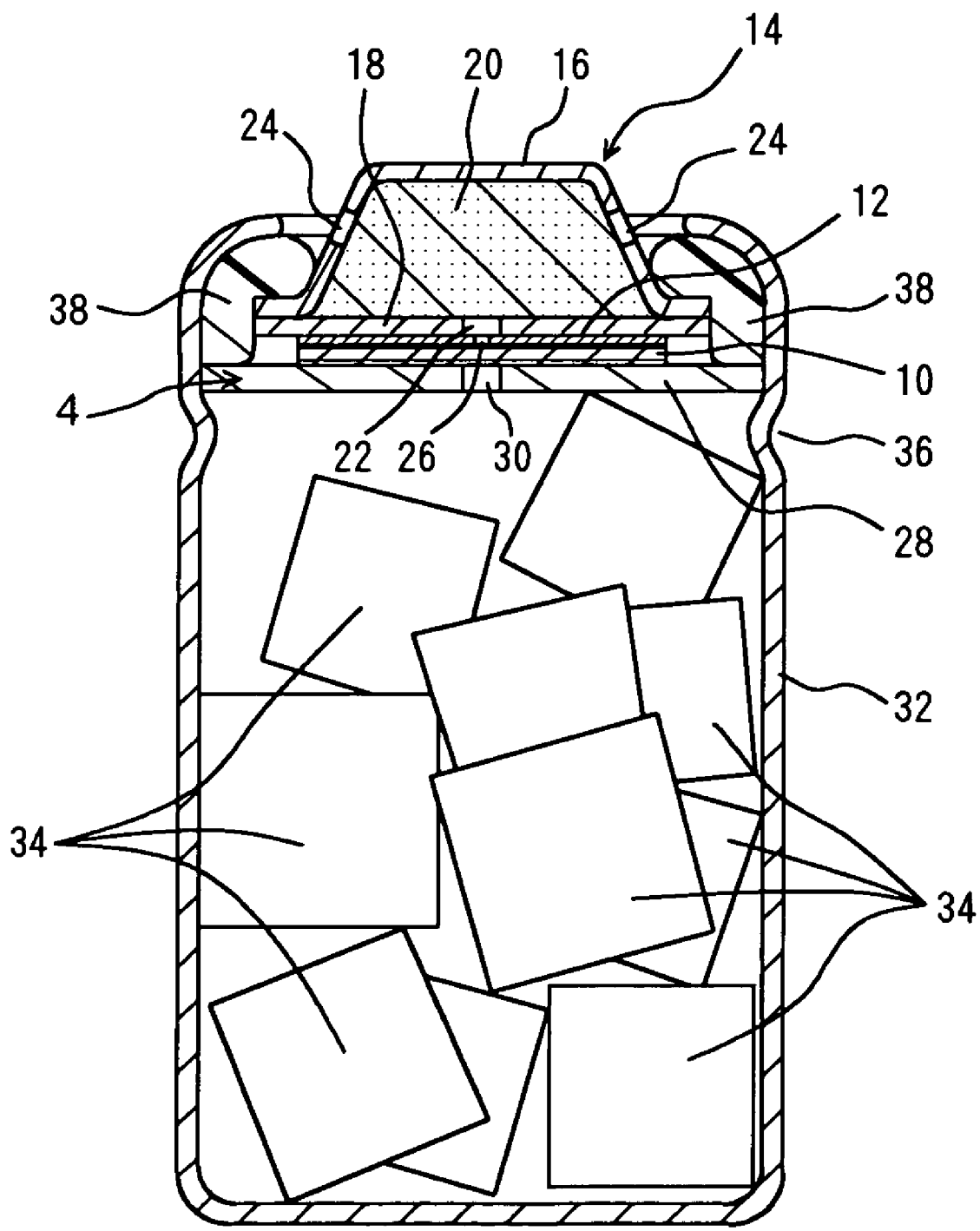
FIG. 1 is a sectional view of the proton conductor gas sensor of an embodiment.
Figure 2:
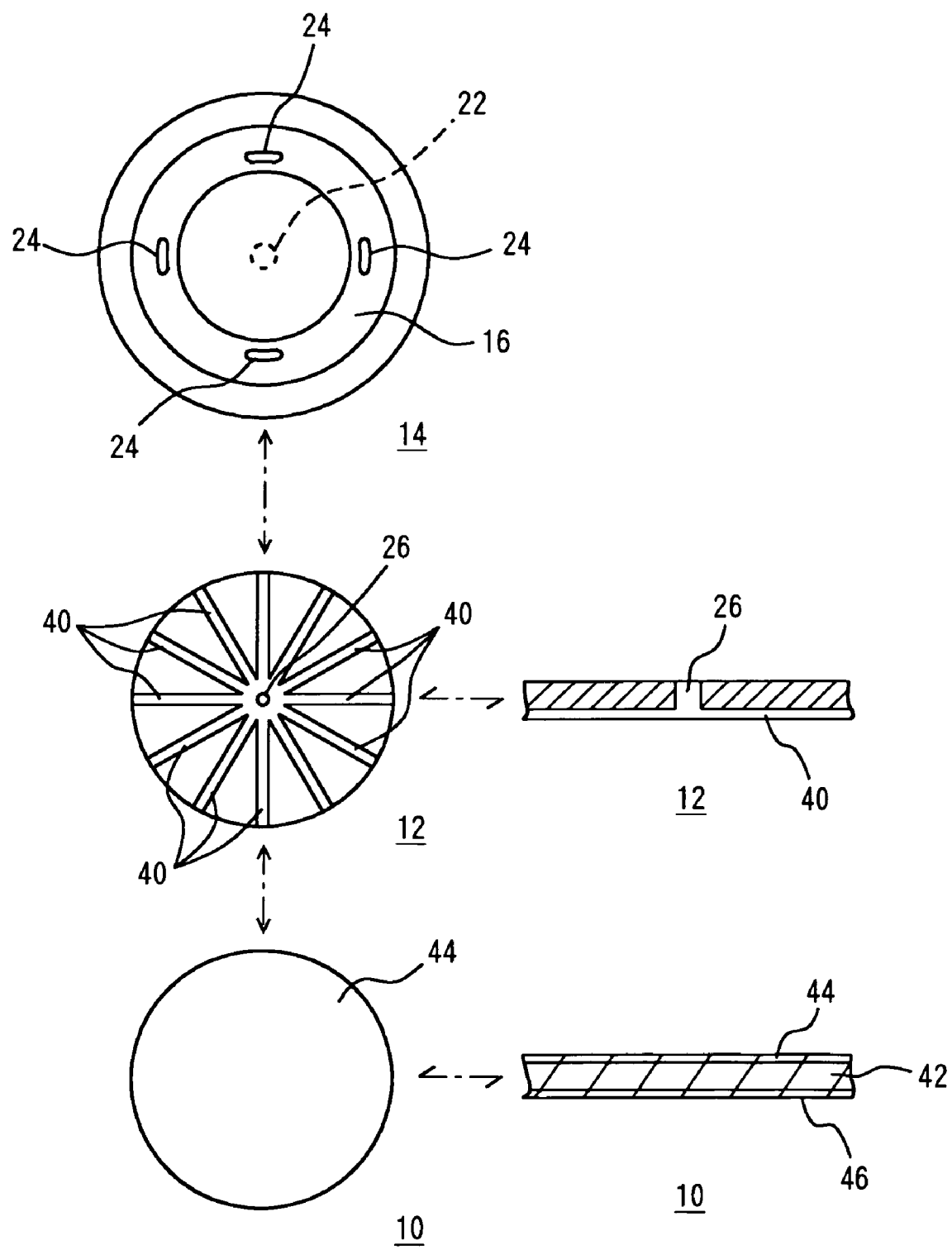
FIG. 2 is a diagram illustrating members, from a cap body to an MEA, of the proton conductor gas sensor of FIG. 1.
Figure 3:
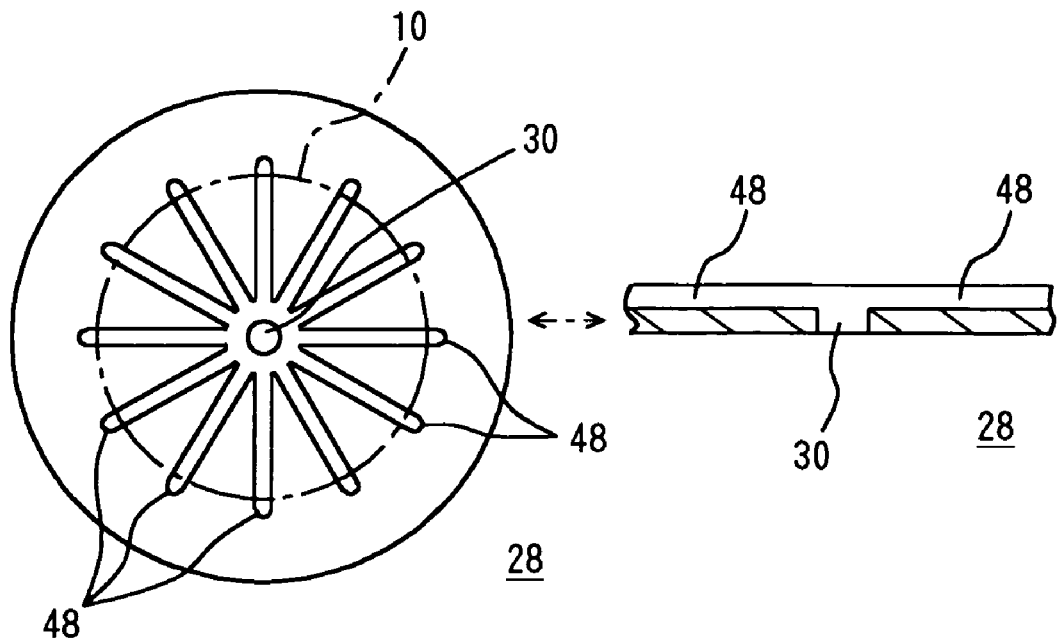
FIG. 3 is a diagram illustrating a lower metal plate of the proton conductor gas sensor of the embodiment, in plan and in section.
Figure 4:
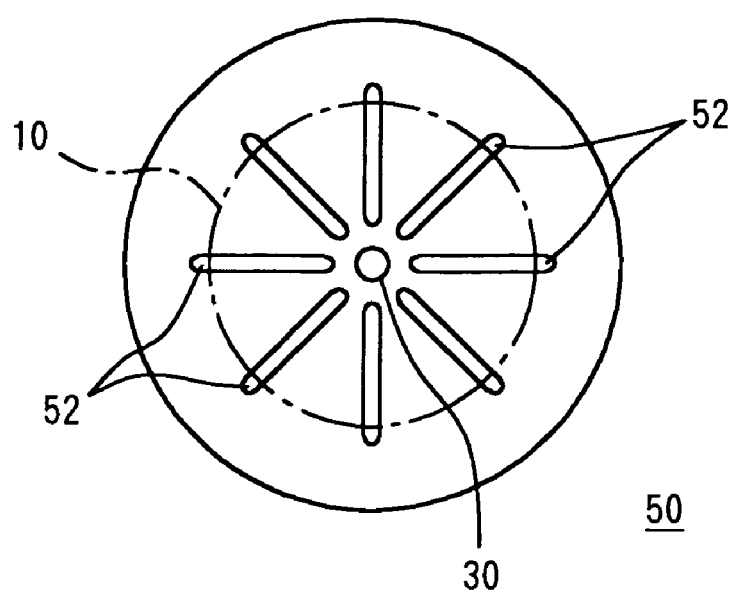
FIG. 4 is a plan view of a lower metal plate of a modification.
Figure 5:
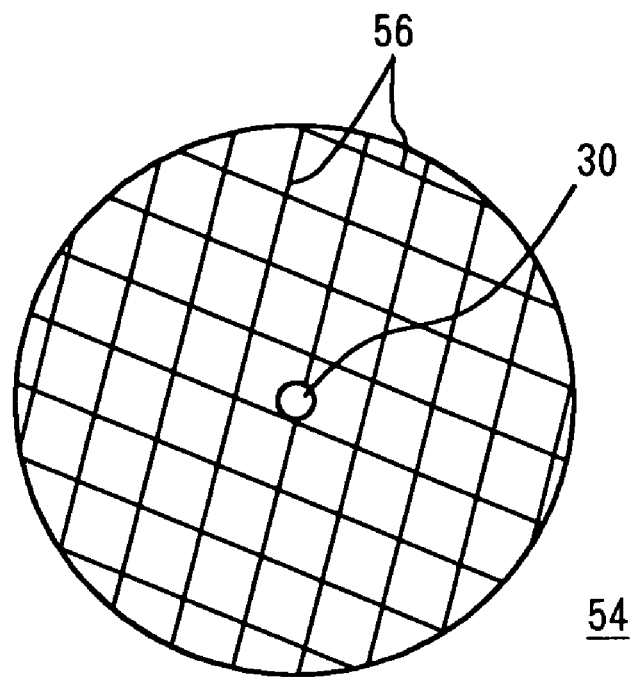
FIG. 5 is a plan view of a lower metal plate of a second modification.

FIG. 1 through FIG. 9 illustrate the embodiment and its modifications. In FIG. 1 through FIG. 3, 2 denotes a proton conductor gas sensor, and 4 denotes a sensor body comprising an MEA 10, a diffusion control plate 12, a cap body 14, and a metal washer 28. The MEA 10 comprises, as shown in FIG. 2, a proton conductive membrane 42, a sensing electrode 44 towards the diffusion control plate 12, and a counter electrode 46 provided towards the washer 28. The locations of the sensing electrode 44 and the counter electrode 46 may be reversed, and in that case, the proton conductor membrane 42 is provided with a through hole to supply the ambient atmosphere to the sensing electrode, and the counter electrode is sealed from the ambient atmosphere. The washer 28 is provided with a water vapor introducing hole 30, described later, to supply water vapor from a water reservoir in this case to the sensing electrode.

The diffusion control plate 12 comprises a thin plate of, for example, stainless steel or titanium, having thickness of, for example about 0.1 mm. The plate 12 is provided with a diffusion control hole 26 of about 0.1 mm in diameter made by punching or the like. In place of the metal diffusion control plate 12, a gas-permeable membrane such as a fluorocarbon resin membrane may be used to effect diffusion control. The cap body 14 is at the upstream of the diffusion control plate 12, and is designed to eliminate poisoning matters and gases that may cause false alarms. The cap body 14 comprises a metal cap 16 and a metal bottom plate 18, and is filled with filter material 20, such as activated carbon, silica gel and zeolite for gas adsorption. This silica gel is the conventional silica gel for gas adsorption, of which silica is of continuous phase. In the conventional silica gel, the amount of water can be held is not more than 10% of the dry weight of the gel. The water retention capacity is defined as the amount of water that can be retained without any leakage for at least one day after the container holding the gel is toppled.

The bottom plate 18 is provided with an opening 22, for example, at the center thereof, and the cap 16 is provided with an opening 24 on the side thereof. The opening 22 and the opening 24 are so arranged that they do not overlap in the axial direction of the cap body 14. It is desirable that at least one of the opening 22 and the opening 24 is provided in plurality. In this way all the area of the filter material 20 is made to function as filters, and in turn, their service life is extended. The washer 28 comprises a metal plate of stainless steel or titanium or the like, of which thickness is thicker than that of the diffusion control plate 12 and is, for example 0.5 mm. The washer 28 is provided with one or plural water vapor introducing holes 30 to supply water vapor from the water reservoir to the counter electrode. The water vapor introducing hole 30 is made larger than the diffusion control hole 26 and is, for example, about 0.5 mm in diameter.

32 denotes a metal can, 34 denotes a gel made of pure water and a gelling agent. The gelling agent is fine particles of silica prepared by the dry method, and the gel is in an appropriate form such as cube or pillar. 36 denotes a concaved part for supporting the metal washer 28, and 38 denotes a gasket between the cap body 14 and the metal can 32. By caulking the upper part of the metal can 32, the sensor body is fixed to the metal can 32. The cap body 14 is insulated from the metal can 32, and electric connection and sealing are effected at various parts of the sensor body 4.

In FIG. 2 and FIG. 3, the structure of various parts of the sensor body is illustrated. The cap body 14 is towards the ambient atmosphere above the diffusion control plate 12, and a large number of grooves 40 connected to the diffusion control hole 26 are arranged, for example, in a radial form, on the bottom face of the diffusion control plate 12 above the MEA 10. The grooves 40 are designed to distribute the ambient atmosphere supplied from the diffusion control hole 26 along the surface of the diffusion control plate 12 to the sensing electrode uniformly. The configuration of the grooves 40 is discretionary. Any form is appropriate provided that the grooves are connected to the diffusion control hole 26 and provide a gas flow channel by concaves and convexes on the surface of the diffusion control plate 12.

On the washer 28, a plurality of grooves 48 are provided so that each groove 48 extends a little outside of an overlapping area with the MEA 10 from the water vapor introducing hole 30. While the grooves 48 are connected to the water vapor introducing hole 30 however like the washer 50 of FIG. 4, the grooves 52 may not be connected to the water vapor introducing hole 30. The grooves 48, 52 are designed to supply hydrogen diffused through the diffusion control hole 26 to the counter electrode from the outside of the MEA 10 along the surface of the washer 28 or the like.

Hydrogen has a large diffusion coefficient and it is hard to seal out hydrogen. Hence hydrogen can reach the grooves 48, 52 along the periphery of the MEA 10. In contrast to it, gases such as CO have smaller diffusion coefficients, and their diffusion via the periphery of the MEA 10 can be neglected virtually. When hydrogen is supplied through grooves 48 or 52 to the counter electrode the hydrogen sensitivity on the sensing electrode and the hydrogen sensitivity on the counter electrode, will be canceled with each other, and thus the relative sensitivity to hydrogen to other gases such as CO can be reduced. Here the gas to be detected is CO, but it may be, for example ammonia or H2S or NOx or SOx. The concaves and convexes provided on the washer are not limited to grooves. They may have any configuration, provided that they provide channels diffuse hydrogen from the periphery of MEA 10 to the counter electrode. For example, in the washer 54 of FIG. 5, knuring-shaped grooves 56 are provided to diffuse hydrogen.

Figure 6:
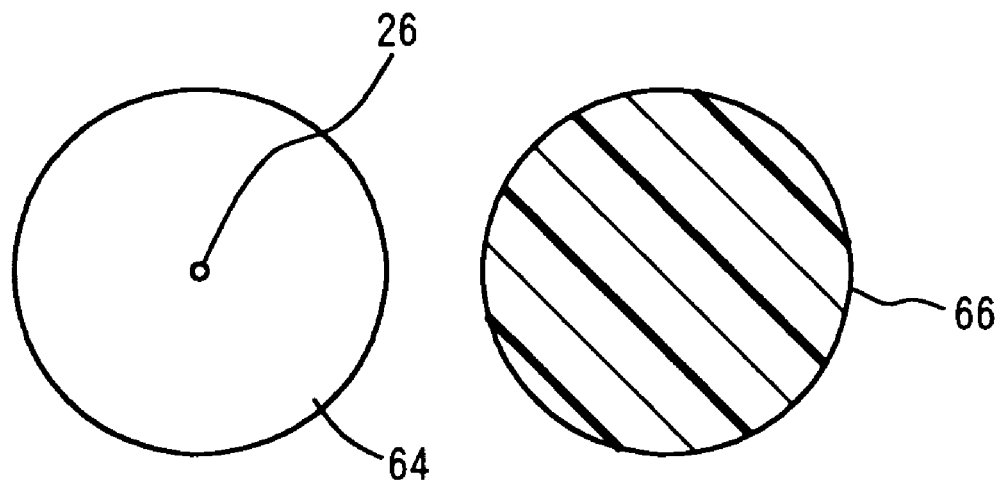
FIG. 6 is a diagram illustrating a diffusion control plate and an upper carbon sheet in the second modification.
Figure 7:
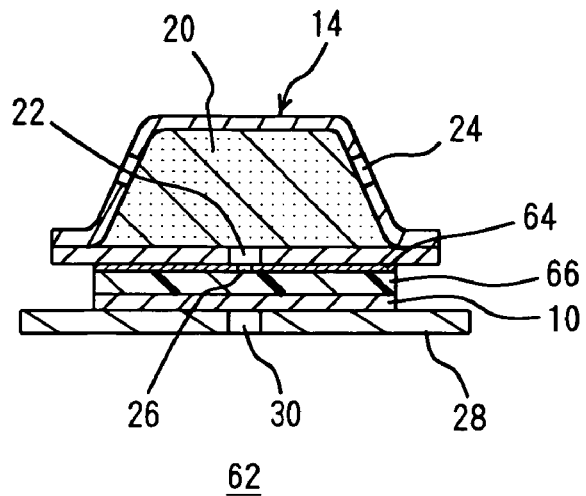
FIG. 7 is a sectional view illustrating a sensor body of the modification of FIG. 6.

In the embodiment, grooves 40 are provided on the diffusion control plate 12 to supply the gas. However, a carbon sheet may be provided between the diffusion control plate 12 and the MEA 10 to supply the ambient atmosphere. Such an example is illustrated in FIG. 6 and FIG. 7. 64 denotes a diffusion control plate of a metal such as stainless steel or titanium, and a diffusion control hole 26 of about 0.1 mm in diameter is provided at the center thereof by punching or the like. If the bottom plate of the cap body 14 is stainless steel and its thickness is, for example 0.5 mm and a diffusion control hole of about 0.1 mm in diameter is made by etching. In this case, a hole having a diameter of ⅕ of the depth is made by etching. This, however, resulted in deficient precision in etching and the standard deviation of the output distribution among the gas sensors was three to four times greater than that of the embodiment of FIG. 6 and FIG. 7. If a diffusion control plate 64 or the like, thinner than the bottom plate of the cap body, is provided independently of the cap body 14 or the like, and a diffusion control hole 26 of which diameter is smaller than that of the opening in the bottom plate is provided by punching, homogeneous output distribution among the gas sensors could be obtained. A carbon sheet 66 is provided between the diffusion control plate 64 and the MEA 10. The carbon sheet 66 is a member having a thickness ranging from about several tens to 100 μm, and is porous, hydrophobic and electro-conductive. A carbon sheet may also be provided between the MEA 10 and the washer 28. In such a case, grooves of the washer 28 or the like are not required.

Figure 8:
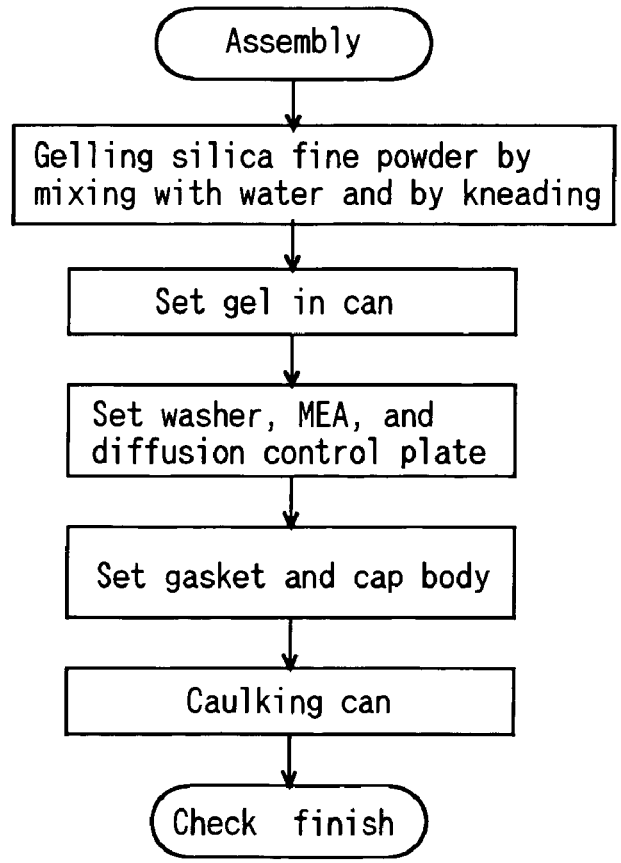
FIG. 8 is a process chart illustrating the assembling process of the proton conductor gas sensor of the embodiment.

FIG. 8 illustrates the assembling procedure of the gas sensor 2. As for fine particles of silica, silica fine particles obtained by the hydrolysis of SiCl4 or the like in vapor phase are used. The particle diameter of these fine particles is from about 5 to 50 nm, and the fine particles are spherical. As the fine particles are obtained by thermal decomposition in vapor phase, the content of Na ion or the like is extremely small, and their bulk density in dry condition is about 50 to 100 g/liter and their specific surface area is about 200 m2 /g. Water is added to the silica fine particles and the mixture is stirred, while being subjected to shearing force, by, for example, an ultramixer of MIZUHO INDUSTRIAL CO. LTD. During this time, the networks of the silica fine particles are broken and their apparent particle diameter is reduced from 10 -100 μm to a smaller value, for example, including those of 1 μm or under. After mixing, when the mixture is left to stand, it gelates due to thixotropy. Due to being kept to stand, the apparent mean particle diameter of the gelling agent increases again to 10 μm or over. This indicates that chains of silica fine particles are broken by mixing, and then when being left to stand, their chains grow again to form three-dimensional networks. It is considered that inside the formed networks, namely in spaces between chains and chains of silica, liquid water is retained. The resulting gel is stable and is not solated even when it is left to stand. The gel as it is or cut into desired forms such as columns or cubes is stored in the metal can. The composition of the gel is, for example, 20 wt % of dry silica fine particles and 80 wt % of water. Above the concaved part of the metal, can the washer the MEA and the diffusion control plate are set, then the cap body and the gasket are set, and the metal can is caulked. Then, the completed gas sensor is inspected.

Figure 9:
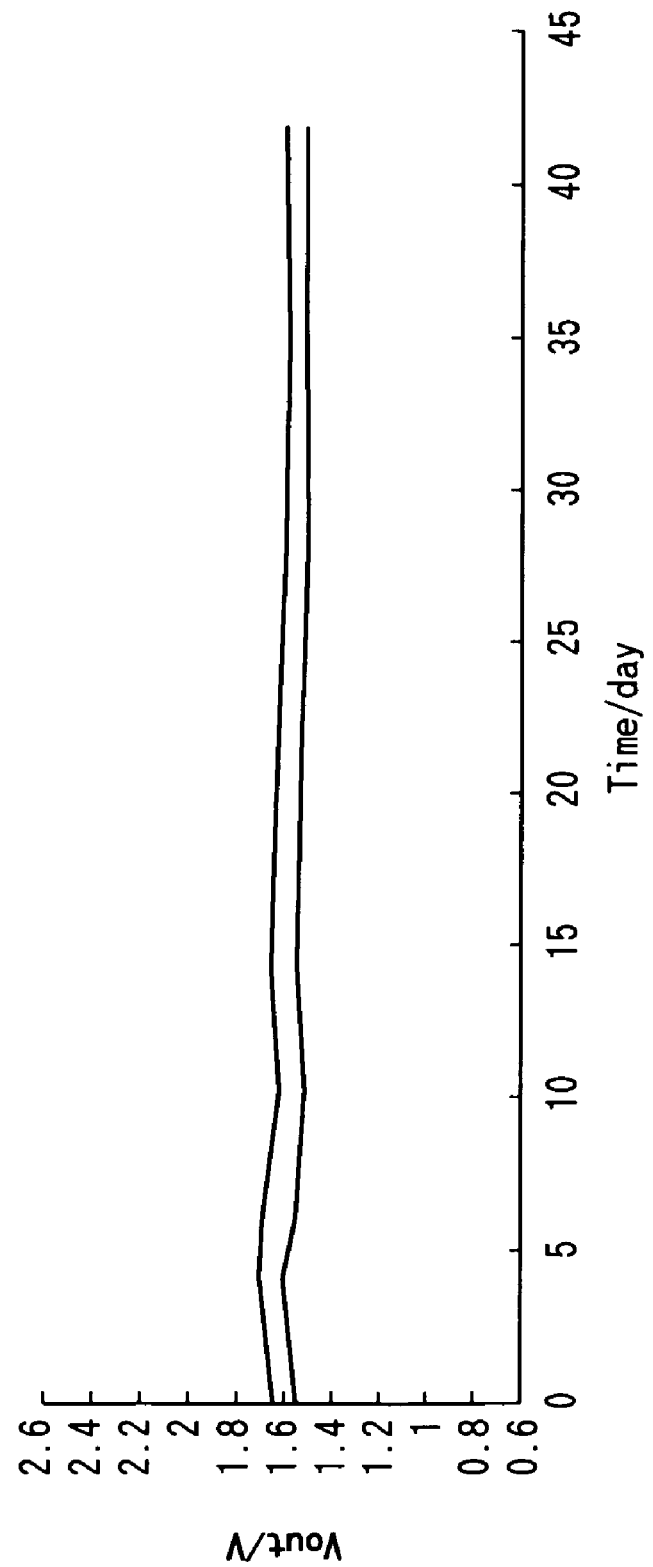
FIG. 9 is a characteristic diagram illustrating the durability characteristics at 70° C. of the proton conductor gas sensor of the embodiment.
Figure 10:
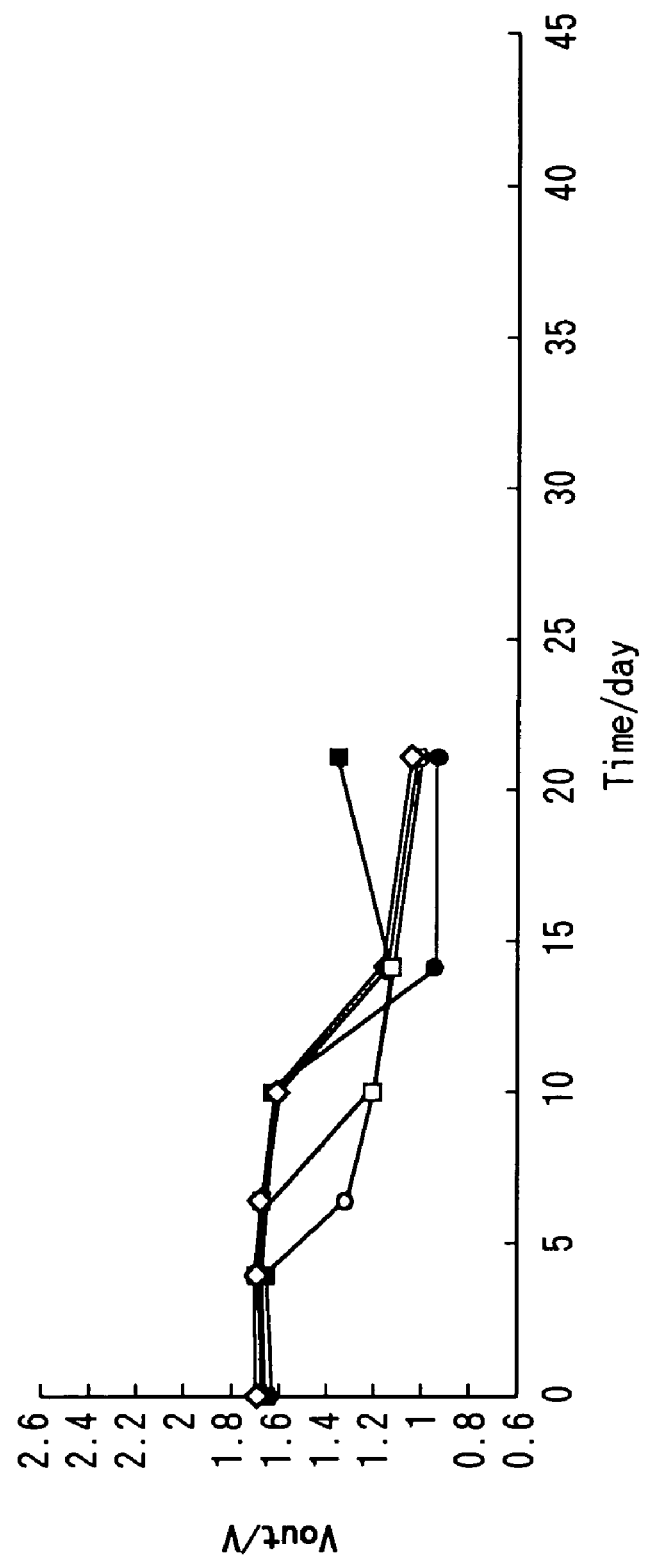
FIG. 10 is a characteristic diagram illustrating the durability characteristics at 70° C. of a conventional proton conductor gas sensor.

FIG. 9 and FIG. 10 illustrate the durability characteristics at elevated temperature of the proton conductor gas sensor. FIG. 9 illustrates the characteristics of the gas sensor 2 of the embodiment of FIG. 1 through FIG. 3. FIG. 9 illustrates the maximum-minimum range of outputs of ten gas sensors. FIG. 10 illustrates the output distribution of five gas sensors using carrageenan as the gelling agent. Carrageenan is a starch polysaccharide.

In the embodiment, water of four times in weight of the gelling agent was added, and in the conventional gas sensor, water of five times in weight of the gelling agent was added. These sensors were kept in an atmosphere of 70° C., and they were taken out into an atmosphere of normal temperature and normal humidity from time to time to measure the output in 300 ppm of CO. The output taken on the ordinate is that of an amplifying circuit, and its unit is in practice arbitrary.

In the embodiment, after passage of 40 or more days in the atmosphere of 70° C., no significant changes were observed in the output. In contrast to it, in the conventional case of FIG. 10, a gas sensor marked a drop in output after about five days, and all the sensors marked significant changes in the output from their initial values after 20 days. Next, after the test of the durability at elevated temperature, the sensors were disassembled to examine the gels. In the embodiment, the gel retained the initial form. In the conventional sensors, the gel lost its initial form and was was solated at the elevated temperature. It is considered that the solated gel penetrated through the water vapor introducing hole into the MEA, and in turn, the sensor characteristics changed.

In addition to the above-mentioned gas sensors, the present inventors experimentally produced gas sensors by using synthetic polymer type gelling agents such as polyacrylic acid. When such gas sensors were subjected to aging at 70° C. for several days or longer, the output corresponding to CO irreversibly dropped. Moreover, synthetic polymer type gelling agents contain a large amount of alkali metal ions such as Na+ ion, and hence if it is solated, the MEA will be contaminated with metal ions.

In the case of a natural polymer gelling agent such as carrageenan, when the gel was touched by fingers and then left to stand at room temperature for one week, growth of miscellaneous bacteria was found all over the gel. In contrast to it, in the case of the gel with silica fine particles as the gelling agent, when it was touched by fingers and then left to stand miscellaneous bacteria grew only on those areas touched, and bacteria did not spread to the remaining areas. This means that when inorganic fine particles are used for a gelling agent as energy sources for miscellaneous bacteria are not contained in the gel, bacteria can not grow. Thus there is no need of adding an antiseptic agent to a gelling agent using inorganic fine particles.

Dry method silica was indicated as an example of gelling agent, but gelling agents are not limited to it. A desirable gelling agent is inorganic fine particles, and therefore there is no need of an antiseptic agent. Moreover it is hardly get solated at elevated temperature, and contents of metal ions such as alkali metal ions and contents of negative ions such as chlorine ion are low, for example, the total content of them is not more than 100 wtppm. Furthermore, its water-holding capacity is high, and for example, the dry weight of the gelling agent in the gel is not higher than 30 wt %, and even if the container of the gel is toppled, the gel will not drip off. From the viewpoint of structure, it is desirable that the fine particles of the gelling agent link in chains to form networks and water is retained inside the networks. In this case, water is present between chains and chains. To this end, it is desirable that water to which a gelling agent is added can be solated by mixing or the like, and then the mixture is gelated by standing or heating thereafter. The gelling agent concentration in the gel at the time of production is, for example from 10 to 30 wt %, and preferably, from 18 to 25 wt %. From the viewpoint of materials, there are gelling agents using dry method silica, and those using dry method alumina, etc.

The conventional silica gel used as a desiccant obtained by hydrolysis of sodium silicate contains a large amount of Na+ ion as an impurity. The amount of water that can be retained is small, namely, not more than 10 wt % of the dry weight of the silica gel. The life of the proton conductor gas sensor depends on the amount of water vapor supplied from the water reservoir, and therefore, it is impractical to use a gel of low water content.

Embodiment 2

Figure 11:
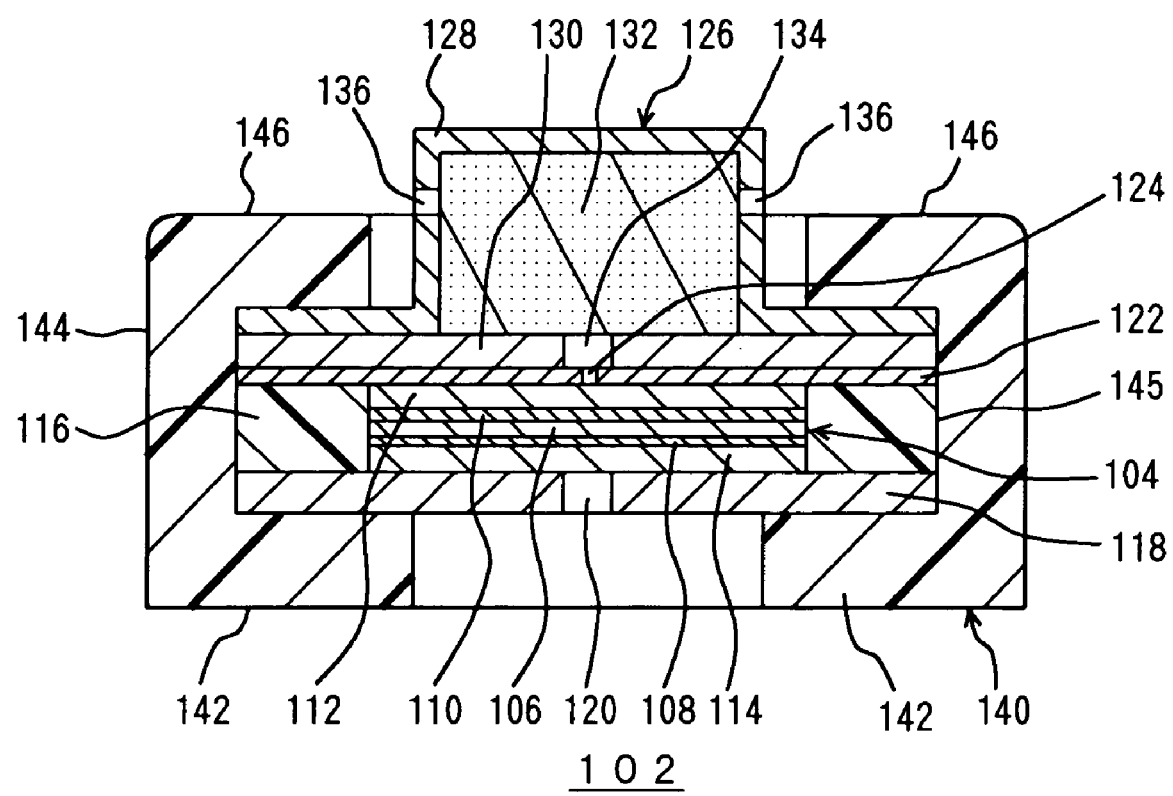
FIG. 11 is a sectional view of the sensor body of the proton conductor gas sensor of the second embodiment.
Figure 12:
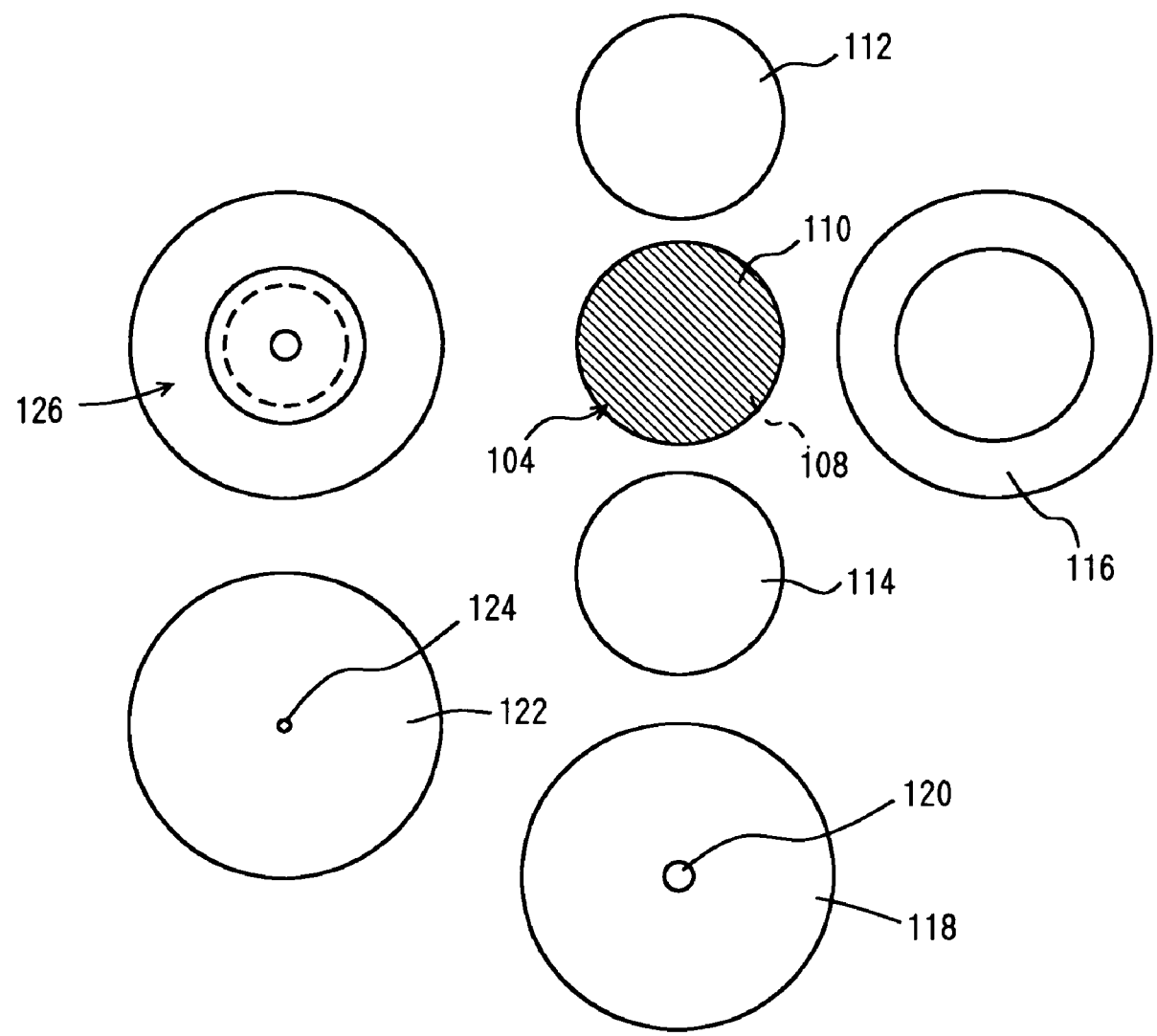
FIG. 12 is a diagram illustrating the sensor body disassembled of the second embodiment.
Figure 13:
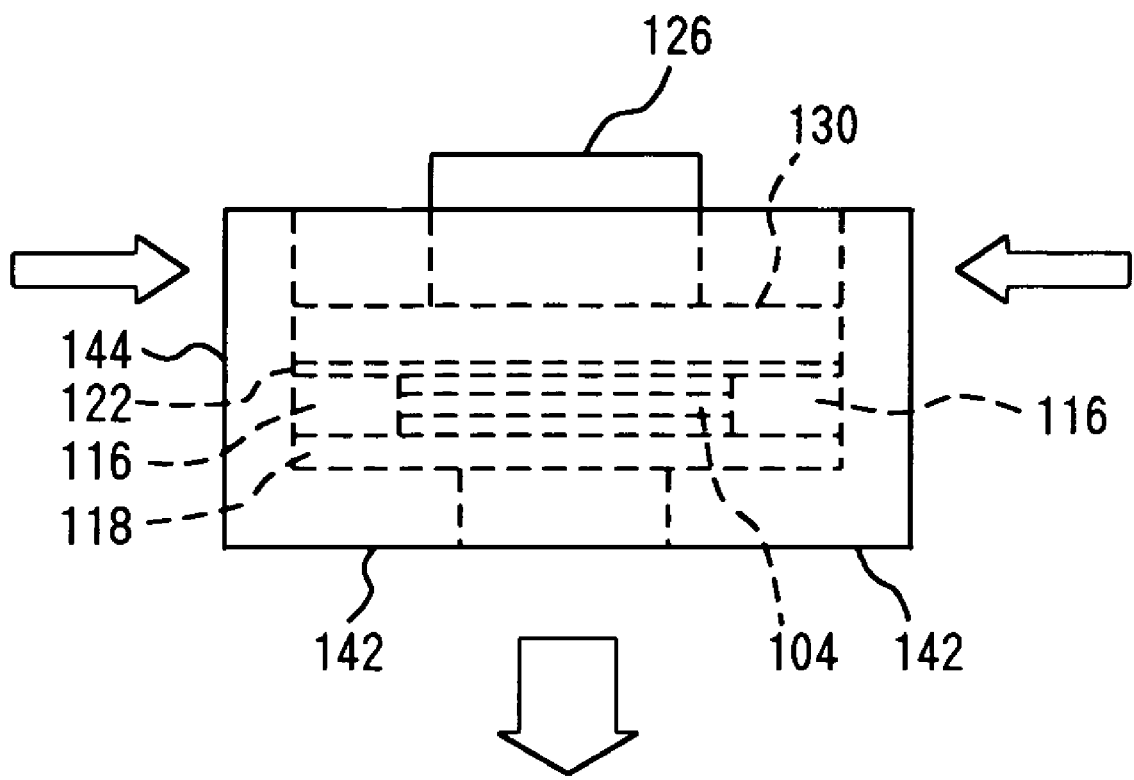
FIG. 13 is a diagram illustrating the assembling process of the sensor body of the second embodiment.
Figure 13:
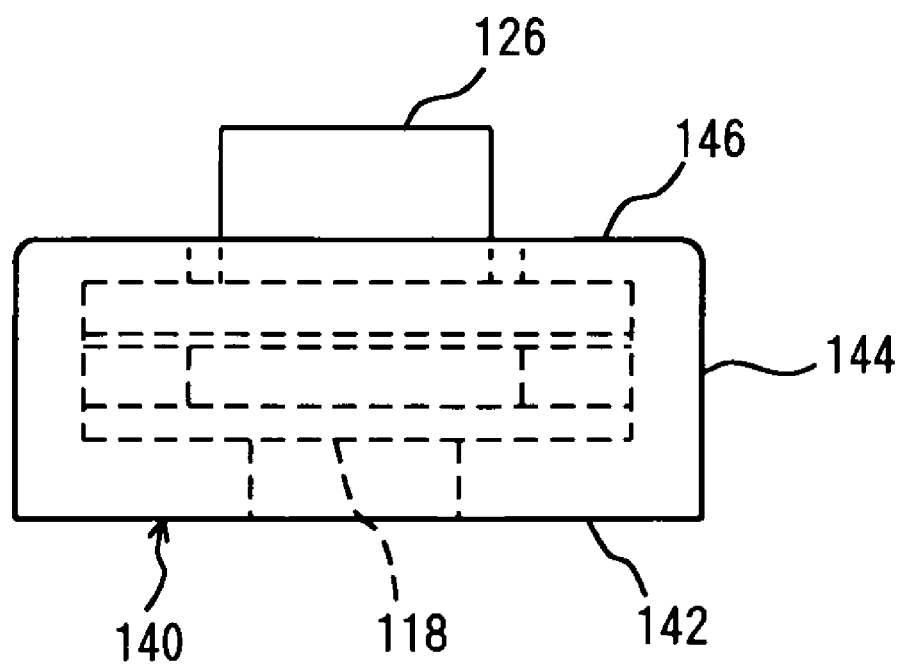

FIG. 11 through FIG. 13 illustrate the second embodiment. In these diagrams, 102 denotes a sensor body having an MEA 10, where a counter electrode 108 is provided on one face of a proton conductive membrane 106 and a sensing electrode 110 is provided on the other face thereof. As for the proton conductive membrane 106, a membrane of a solid polymer proton conductor or the like is used. A carbon film 112 is laid on the sensing electrode 110 of the MEA 104, and a carbon film 114 is laid on the counter electrode 108 thereof. The carbon films 112, 114 are, for example, electro-conductive and porous membranes, porous carbon sheets made hydrophobic with fluoro-carbon resin or the like. The carbon films 112, 114 distribute gas to the sensing electrode 110 and the counter electrode 108 and provide electro-conductive contacts with metal plates 118, 122, described later. The carbon film 112 on the sensing electrode 110 distributes gas in the atmosphere to the sensing electrode 110, and the carbon film 114 on the counter electrode 108 distributes also water vapor from the water reservoir to the counter electrode 108. The carbon film 114 on the counter electrode 108 may be omitted.

116 denotes a ring-shaped elastic body, and for example, elastomer of polyurethane is used. 118 and 122 denote metal plates, for example, thin plates of stainless steel or titanium. 120 denotes an opening made in the metal plate 118 below the counter electrode 108. The opening 120 introduces water vapor, for example, from the water reservoir shown in FIG. 1. 124 denotes a diffusion control hole provided in the metal plate 122 above the sensing electrode 110. The elastic body 116 seals the rim of the MEA 104 between the metal plates 118 122 to prevent the ambient atmosphere from reaching the counter electrode 108, though the sensing electrode 110 or through the gaps between the sensor body housing 140, explained later, and the metal plates 118, 122.

The metal plate 118 below the counter electrode 108 is, for example, about 0.5 mm thick. Its opening 120 is, for example, about 0.5 mm in diameter, and is formed by etching or punching with a press. The diffusion control hole 124 is made with good precision in diameter. The hole 124 is smaller than the opening 120. The metal plate 122 above the sensing electrode 110 is formed from, for example, a metal plate of about 0.1 mm in thickness, thinner than the metal plate 118, and the diffusion control hole 124 is made by punching with a press so as to keep the hole diameter precisely uniform. As the metal plate 122 is thin the diffusion control hole 124 may be formed by etching, but dispersion in the hole diameters will increase due to overetching or underetching.

126 denotes a cap body comprising a metal cap 128 and a lower metal plate 130. A filter material 132 such as activated carbon, silica gel and zeolite is filled in the space between them, and the ambient atmosphere is supplied through gas introducing holes 134, 136 to the diffusion control hole 124. Poisoning gases and gases causing false alarm are eliminated by the filter material 132. At least one of the gas introducing holes 134, 136 is arranged away from the axial center of the cap body 126. Here the gas introducing hole 134 is arranged at the axial center of the cap body 126, and a plurality of gas introducing holes 136 are provided in the side face of the metal cap 128. In this way, the entire filter material 132 is arranged to be used, and in turn the service life is extended. It may be possible not to provide the lower metal plate 130; a metal plate 122 with a diffusion control hole 124 may be directly mounted at the bottom of the cap 128 by, for example welding.

140 denotes a sensor body housing of a resin. It is a ring-shaped member, and the resin material is, preferably, a thermoplastic resin; for example, polypropylene, ABS, nylon, acrylic resin or polycarbonate. A thermosetting resin may be used for the sensor body housing 140, but it is hard to mold the resin into a ring-shaped form before thermal deformation. A rubber-like resin may be used for the sensor body housing 140, and the metal plates 118, 122 may be arranged to be pressed from above and below by elastic forces of the rubber. However, a rubber-like resin might generate gas when exposed to elevated temperature of about 70° C. and affect the MEA 104.

142 denotes the bottom part of the sensor body housing 140, molded in such a form from the initial molding of the sensor body housing 140. 144 denotes the side part, and 145 denotes a groove part on the inner side of the side part 144. 146 denotes a top part provided by thermal deformation when assembling the sensor body 102. The sensor body housing 140 holds the metal plate 118 and the lower metal plate 130, and so on, in the groove part 145 on the inner side of the side part 144, and the parts held therein are sandwiched by a pair of flanges, namely, the bottom part 142 and the top part 146. Those parts of the cap body 126 and the metal plate 118, etc. are fixed by compression force between the bottom part 142 and the top part 146 and at the same time, airtightness and electric connections of these parts are secured.

When the upper part of the sensor body housing 140 is heated to around the softening temperature of the thermoplastic resin and forces are applied towards the cap body 126, the upper part of the sensor body housing 140 will undergo thermal deformation to provide the top part 146. When cooling down thereafter, the top part 146 tends to shrink, and in turn generate compression force working along the direction from the top part 146 towards the bottom part 142. The compression force secures electric contacts between the lower metal plate 130 and the metal plate 122, between the metal plate 122 and the carbon film 112, and between the carbon film 112 and the sensing electrode 110. Similarly, the force secures electric contacts between the metal plate 118 and the carbon film 114, and between carbon film 114 and the counter electrode 8. Moreover, the force between the top part 146 and the bottom part 142 secures airtightness, which for example prevents gas from migrating along the rim of the lower metal plate 130 or the rim of the metal plate 118.

As the sensor body 102 is fixed by using the compression force that is generated after thermal deformation of the top part 146, unlike caulking, no impact is given. According to the experience of the present inventors, when the MEA 104, the carbon films 112, 114, etc. were positioned between the metal plates 118, 122 by caulking, displacement of the carbon films 112, 114 or the MEA 104 occurred at a frequency of about 5%. The sensors having such a displacement are rejected. When thermal deformation is used, as mechanical impacts are not exerted, such defects will not occur. Moreover, pressing through the use of the contractive force after thermal deformation can apply pressure almost evenly along the circumferences of the lower metal plate 130 and the metal plate 118.

FIG. 12 illustrates the disassembled state of the major parts of the sensor body 102. The carbon film 112 is close to the sensing electrode 110 of the MEA 104, and the carbon film 114 is close to the counter electrode 108 thereof. The carbon films 112, 114 and the MEA 104 are members of which membrane thicknesses are about several tens μm, and they have the same diameter. The ring-shaped elastic body 116 surrounds them. The thick metal plate 118 is beneath the carbon film 114, and the thick metal plate 118 is provided with the opening 120 of which diameter is large. In contrast to it, the thin metal plate 122 is above the carbon film 112, and the metal plate 122 is provided with the diffusion control hole 124 made by punching. The hole 124 has a diameter of about 0.1 mm. The cap body 126 is arranged over the metal plate 122.

FIG. 13 illustrates the assembling process of the sensor body 102. The MEA 104, carbon films 112, 114, metal plates 118, 122 and the cap body 126 are set on the bottom part 142 of the housing. Next, the upper part of the housing is heated and pressed towards the lower metal plate 130, the top part 146 will be formed by thermal deformation. This completes the assembly into the sensor housing body 140. When the housing 140 cools down the compression force will be generated between the bottom part 142 and the top part 146 by the contraction in the top part 146. The respective members of the sensor body 102 are positioned by the force and electric contacts and necessary airtightness are secured.

In the embodiment, the bottom part 142 is formed beforehand, and the top part 146 is thermally deformed during assembling the sensor body 102. However, conversely, the top part 146 may be formed beforehand, and then the bottom part 142 may be thermally deformed during assembling the sensor body. The cap body 126 is a member for storing the filter materials 132 and may be omitted. Moreover, it is not necessary to integrally assembling the cap body 126 together with the metal plates 118, 122 into the sensor body housing 140.

The invention claimed is:

1. A proton conductor gas sensor comprising:
   a sensor body having a membrane electrode assembly (MEA) comprising an electrolyte membrane, a sensing electrode, and a counter electrode, and a water reservoir positioned at one side of the sensor body and supplying water vapor to the membrane electrode assembly;
   a cap body including a cap, a bottom plate, and filter material provided between said cap and said bottom plate, said cap having at least one first opening and said bottom plate having a second opening for introducing ambient atmosphere towards said membrane electrode assembly from an opposite side of the membrane electrode assembly to the water reservoir; and
   a thin nonporous, metal plate between said bottom plate and said membrane electrode assembly, having a diffusion control hole connected to the second opening of the bottom plate and having a smaller diameter than that of the opening of the bottom plate.

2. The proton conductor gas sensor of claim 1, wherein said diffusion control hole is made mechanically by a punching process.

3. The proton conductor gas sensor of claim 1, wherein said MEA further comprising a first carbon film disposed on said sensing electrode and a second carbon film disposed on said counter electrode.

4. The proton conductor gas sensor of claim 3, wherein said first and second carbon films are porous for distributing gases to the sensing and counter electrodes.

5. The proton conductor gas sensor of claim 1, wherein said bottom plate and said cap are connected at a periphery of said bottom plate, and said thin nonporous, metal plate is connected on a first side with said bottom plate and on a second side with said MEA, thereby providing an electrical path from said MEA to said cap.

* * * * *